United States Patent [19]

Savino

[11] 4,364,507

[45] Dec. 21, 1982

[54] VARIABLE CLOSURE SURGICAL STAPLING APPARATUS WITH RETRACTABLE ANVIL

[76] Inventor: Dominick J. Savino, 65 Buttonwood Rd., Staten Island, N.Y. 10304

[21] Appl. No.: 246,145

[22] Filed: Mar. 23, 1981

[51] Int. Cl.³ .................. B25C 5/04; A61B 17/04
[52] U.S. Cl. ................................ 227/83; 227/19; 227/DIG. 1; 227/155
[58] Field of Search .............. 227/19, 83, 88, 90, 227/120, 123, 127, 129, 155, DIG. 1

[56] References Cited

U.S. PATENT DOCUMENTS

| | | | |
|---|---|---|---|
| 1,945,377 | 1/1934 | Posnack | 227/83 |
| 3,889,683 | 6/1975 | Kapitanov et al. | 227/19 |
| 3,917,145 | 11/1975 | Graf et al. | 227/90 |
| 4,013,206 | 3/1977 | Lemos | 227/123 X |
| 4,127,227 | 11/1978 | Green | 227/19 |
| 4,162,678 | 7/1979 | Fedotov et al. | 227/19 |
| 4,179,057 | 12/1979 | Becht et al. | 227/120 X |
| 4,184,622 | 1/1980 | Spehrley, Jr. | 227/123 X |
| 4,198,982 | 4/1980 | Fortner et al. | 227/19 X |
| 4,216,890 | 8/1980 | Akopov et al. | 227/19 |

Primary Examiner—Paul A. Bell
Attorney, Agent, or Firm—Hedman, Casella, Gibson & Costigan

[57] ABSTRACT

A surgical stapling apparatus is disclosed for suturing skin with deformable staples. The apparatus includes a pivoting anvil having a crescent-shaped configuration. The lower end of the anvil includes a forming lip which is disposed in the drive track of the apparatus. A driver blade is mounted for reciprocal movement in the drive track and includes a lower edge configured to cooperate with the forming lip to clinch the staple. An anvil release blade is disposed behind and coplanar with the driver blade in the drive track. The anvil release blade permits the release of the staple at any stage in the clinching operation. In use, upon downward actuation of the driver blade, the staple is clinched about the forming lip. To release the staple from the apparatus, the anvil release blade is lowered until an aperture located therein is aligned with an aperture provided in the driver blade thereby enabling the anvil to pivot, clearing the drive track. The subject stapling apparatus may be rapidly operated with one hand and is arranged to substantially prevent jamming.

11 Claims, 6 Drawing Figures

VARIABLE CLOSURE SURGICAL STAPLING APPARATUS WITH RETRACTABLE ANVIL

BACKGROUND OF THE INVENTION

The subject invention relates to a surgical stapling apparatus for suturing skin with deformable staples. More specifically, the subject invention discloses a stapler which is relatively simple in construction and permits the release of a staple at any point in the closure operation. In addition, the structure of the subject stapler substantially inhibits jamming.

In most surgical procedures, suturing of incisions or wounds is required. For many years, suturing was accomplished using filiment-type stitches which are individually tied. As can be appreciated, surgical procedures which require a large number of individually tied sutures take a considerable amount of time. It is well known that minimizing the duration of an operation is highly desirable due to the inherent risks of anesthesia.

Accordingly, in the prior art there has been developed surgical staplers which utilize deformable metal staples in place of filiment-type sutures. The advantage of the surgical staplers lies essentially in their fast operational speed enabling the duration of the surgical procedure to be substantially reduced. Examples of some prior art surgical staplers can be found in U.S. Pat. Nos. 3,889,683, issued June 17, 1975 to Kapitanov et al; 4,162,678, issued July 31, 1979 to Fedotov et al; 4,198,982, issued Apr. 22, 1980 to Fortner et al; and 4,216,890, issued Aug. 12, 1980 to Akopov et al.

The above cited patents disclose surgical staplers which are particularly suited for suturing internal organs. Examples of prior art staplers which are more particularly suited to the suturing of skin or fascia can be found in U.S. Pat. Nos. 4,127,227, issued Nov. 28, 1978 to Green, and 4,179,057, issued Dec. 18, 1979 to Becht et al. In a suturing operation and in particular skin suturing, the manner of joining the skin is particularly critical. More specifically, when closing an incision, it is desirable to draw the opposed edges of the skin into abutting contact. As opposed to overlapping the edges or leaving a space therebetween, bringing them into abutting contact promotes healing and minimizes scarring. Suturing with a prior art skin stapler, wherein a staple is clinched causes the skin to be drawn together a fixed amount assuming the skin is sufficiently loose. Thus, in order to achieve the desired abutting configuration, it is necessary that the initial separation, between the edges of the skin be regulated prior to the start of the clinching operation. Stated differently, the initial separation between the edges of the incision must correspond to the amount which the apparatus will draw the skin together.

As can be appreciated, during an operation, the rapid regulation of the separation between the edges of the incision, prior to suturing, may be difficult to achieve. Accordingly, it would be desirable to provide a surgical stapling apparatus which will effectively operate without precisely regulating the separation between opposed edges of an incision.

This object is achieved in the subject invention by providing a unique skin suturing apparatus wherein the clinching of the staple can be halted at any point in the clinching operation. More specifically, during the stapling operation, when the edges of the incision have been drawn together to achieve the desired abutting configuration, the anvil can be retracted releasing the staple in a partially clinched condition.

In the prior art a variety of staplers are known that are primarily intended for use with paper goods, and which incorporate a retractable anvil. Two examples of prior art stapling devices having retractable anvils can be found in U.S. Pat. Nos. 3,917,145, issued Nov. 4, 1975 to Graf et al and 4,013,206, issued Mar. 22, 1977 to Lemos. Both of the patents disclose devices wherein the retraction of the anvil is dependent upon the movement of the driver blade and are incapable of ejecting a partially clinched staple.

Another example of a prior art stapler can be found in U.S. Pat. No. 1,945,377, issued Jan. 30, 1934 to Posnack. The device in Posnack, primarily intended for use with paper goods, includes an embodiment having a retractable anvil which may be operated independent of the driver blade. The Posnack device includes a slidable anvil mounted at the base thereof. A handle may be provided which is pivotally mounted for rotational movement in conjunction with a cam. The cam is in turn, in operational contact with a pivotally mounted anvil actuator. The anvil actuator includes an arm which is in contact with a pin connected to the anvil. In operation, the handle which projects outwardly from the front of the apparatus, is lifted, causing the rotation of the cam which in turn moves the anvil actuator in order to retract the anvil. While the mechanism disclosed in Posnack is intended to be utilized at the end of the drive stroke, it appears that the mechanism could be actuated at an intermediate point to halt the clinching action and release the staple. However, it is clear that the mechanism in Posnack has shortcomings which render it undesirable for use in a surgical stapling apparatus. For example, the anvil mechanism in Posnack is disposed at the base of the apparatus and therefore would retract along the length, and possibly within, the incision. Clearly, this could interfere with the suturing operation and could affect the sterility of the procedure. In addition, due to the arrangement of the pivotally connected handle, which projects outwardly from the front of the device, and must be rotated, it is apparent that the apparatus requires two hands for its operation. More particularly, while one of the surgeon's hands is utilized to actuate the downward movement of the driver blade, his other hand would be required to rotate the handle in order to release the staple.

Accordingly, it is an object of the subject invention to provide a new and improved surgical stapler which is relatively simple in construction and permits the variable clinching of staples.

It is another object of the subject invention to provide a new and improved surgical stapler which can be readily operated with one hand.

It is a further object of the subject invention to provide a new and improved surgical stapler having a retractable anvil which pivots immediately away from the patient's skin surface.

It is still another object of the subject invention to provide a new and improved surgical stapler which includes a means to prevent clogging of staples in the drive track.

SUMMARY OF THE INVENTION

In accordance with these and other objects, the subject invention provides for a surgical stapling apparatus for suturing skin with deformable staples. More specifically, the subject stapler includes a pivotally mounted retractable anvil having a crescent shaped configuration. The lower end of the retractable anvil includes a forming lip which is disposed in the drive track of the apparatus. A driver blade is mounted for reciprocal movement in the drive track and includes a lower edge configured to cooperate with the forming lip of the anvil for clinching the staples. In accordance with the subject invention, an anvil release blade is disposed within the drive track in coplanar relationship with the driver blade. The anvil release blade is operative to permit the release of a staple at any stage of the clinching operation.

In use, upon the downward actuation of the driver blade, the staple is clinched about the forming lip. To release the staple from the apparatus, the anvil release blade is lowered until an aperture located therein is aligned with an aperture provided in the driver blade. The alignment of the apertures in the blades enables the anvil to pivot, moving the forming lip out of the drive track, releasing the staple. The dual, coplanar blade arrangement permits rapid operation of the device with one hand. The subject stapler is relatively simple in construction having a minimum of moving parts such that it is highly reliable. Another unique advantage achieved by the dual blade pivoting anvil arrangement of the subject invention is that jamming of the staples in the drive track is substantially inhibited. More particularly, after the driver blade begins its downward stroke, the top portion of the anvil functions to prevent the driver blade from returning to its initial position until the staple has been released from the drive track. By this arrangement, a second staple is not permitted to enter the drive track until the latter is clear, thereby preventing jamming.

Many other objects and advantages will become apparent from the following detailed description when taken in conjunction with the drawings in which:

DESCRIPTION OF THE PREFERRED EMBODIMENT

Figure 1:
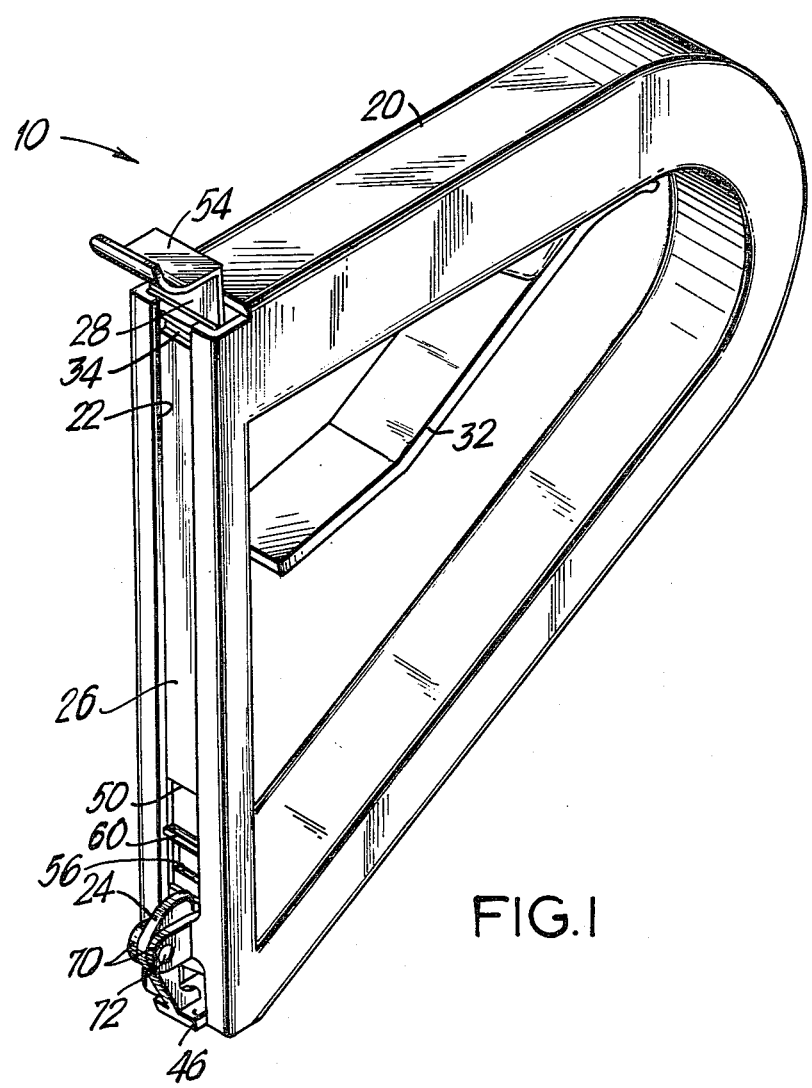
FIG. 1 is a perspective view of the new and improved surgical stapler of the subject invention.
Figure 2:
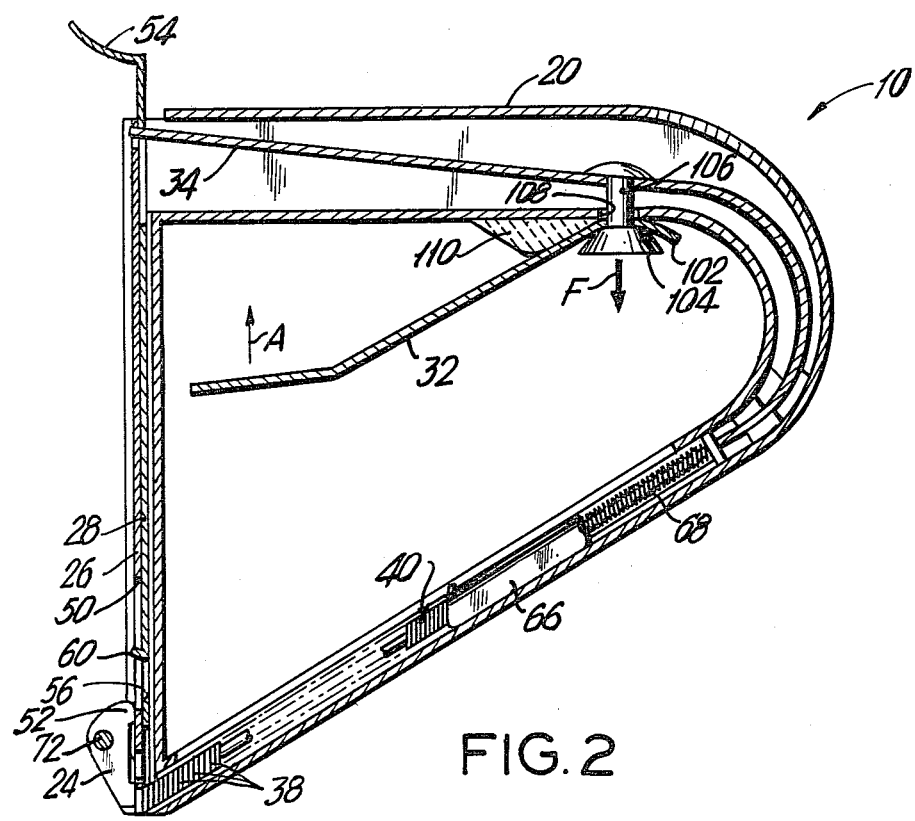
FIG. 2 is a sectional view of the new and improved surgical stapler of the subject invention.

Referring to FIGS. 1 and 2, the surgical stapling apparatus 10 of the subject invention is illustrated. More specifically, the apparatus 10 is defined by a triangular housing 20 which includes a drive track 22. A generally crescent shaped anvil 24 is pivotally mounted to the housing 20 adjacent the lower end of the drive track 22. A driver blade 26 is mounted for reciprocal movement in the drive track 22. In addition, an anvil release blade 28 is reciprocally mounted in the drive track, in coplanar relationship with and behind the driver blade 26. A handle lever 32 mounted within the open area of the housing 20 is connected to an actuator blade 34. Actuator blade 34 is operatively connected to the driver blade 26. A means for feeding staples 38 to the lower end of the drive track 22 is also provided and includes a staple magazine 40.

Figure 4:
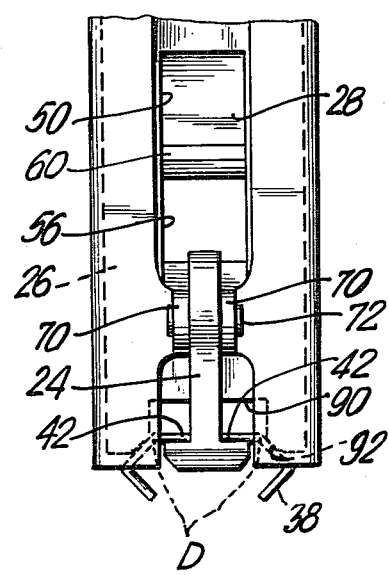
FIG. 4 is a partial frontal view of the new and improved skin stapler of the subject invention, illustrating a partial clinching stage.
Figures 3, 5:
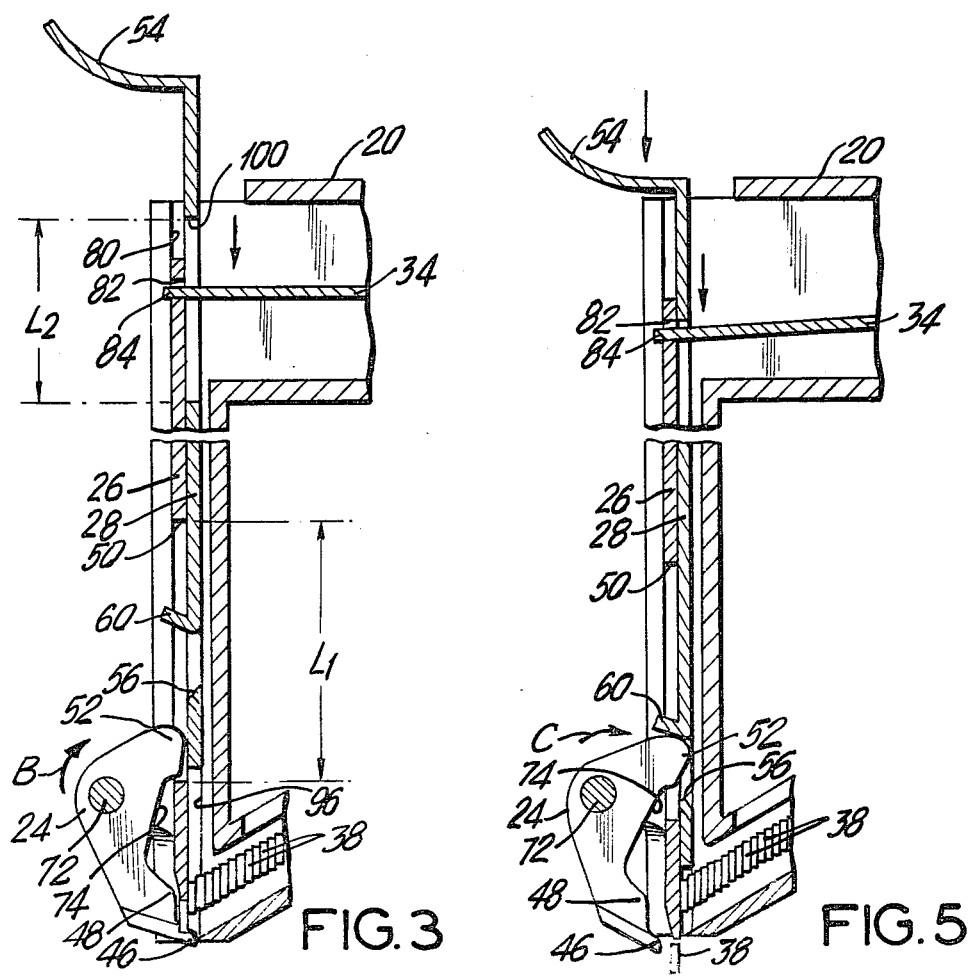
FIG. 3 is an enlarged sectional view of the new and improved surgical stapler of the subject invention, illustrating the initiation of the clinching operation.
FIG. 5 is an enlarged sectionsl view of the new and improved skin stapler of the subject invention, illustrating the release of a staple.

In use, the driver blade 26 is downwardly actuated by upwardly moving lever 32 in the direction of arrow A, in FIG. 2. As illustrated in FIGS. 3 and 4, as the driver blade 26 moves downwardly, the lower end thereof bears on the crown 42 of the lead staple 38 in the drive track, pushing the staple downwardly towards the forming lip 46 of the anvil 24. The lower end of the driver blade 26 is provided with a deforming configuration which cooperates with the forming lip 46 of the anvil to clinch the staple 38.

As illustrated in FIG. 3, in the initial portion of the downward stroke of the drive blade, an aperture 50 provided in the latter becomes aligned with a locking projection 52 formed on the opposed end of the anvil. The downward force placed on the lower portion 48 of the anvil by the driver blade and the lead staple creates a rotational moment which causes the anvil to pivot, in the direction of arrow B, until locking projection 52 abuts the lower end of the anvil release blade 28. The insertion of the locking projection 52 into aperture 50 of the driver blade functions to prevent the premature retraction of the driver blade prior to the release of the staple 38. More specifically, even if the lever 32 is released causing an upward retracting force to be transmitted to the driver blade, the locking projection 52 will prevent the driver blade from moving upwardly. By this arrangement, and as more fully described hereinafter, a second staple cannot be fed into the drive track until the primary staple is released such that jamming is prevented.

Figure 6:
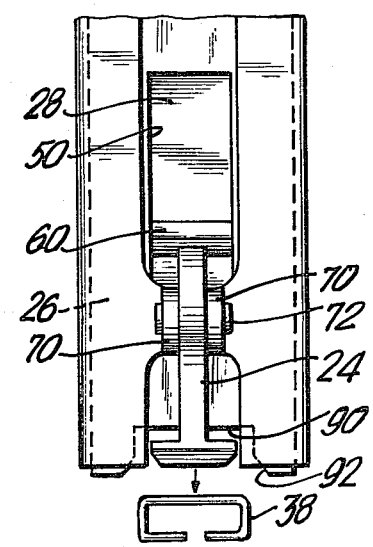
FIG. 6 is a partial frontal view of the skin stapler of the subject invention, illustrating the release of a staple.

As the driver blade 26 moves downwardly through the drive track 22, the degree of clinching of the staple 38 is increased until a configuration, as illustrated in FIG. 6, is achieved. When used in a surgical operation, the edges of an incision are drawn together by the staple as it is clinched. When the desired abutting configuration of the edges of the incision is achieved, the clinching procedure could be stopped and the staple released. In accordance with the subject invention, the staple can be readily released with the desired degree of clinching by downwardly actuating the anvil release blade 28. Anvil release blade 28 preferably includes a plunger type configuration 54 at the upper end thereof so that it may be actuated by the thumb of the user. The downward actuation of the anvil release blade 28 functions to align an aperture 56 provided therein with the aperture 50 provided in the driver blade 26, as illustrated in FIG. 5. Since there is a constant rotational moment on the anvil from the force of the driver blade and the staple in the drive track, the alignment of the apertures (50,56) permits the anvil to fully pivot, in a direction of arrow C, such that the forming lip 46 is withdrawn from the drive track enabling the staple to be released. Preferably, a tang 60 is provided at the upper end of aperture 56 to facilitate the full pivoting of the anvil. As can be appreciated, since the operation of the anvil release blade 28 is independent of movement of the driver blade, any desirable degree of clinching of the released staple can be achieved. By this arrangement, a surgeon actuates the driver blade until the edges of the skin are together. Then the anvil release blade 28 is actuated releasing the full or partially clinched staple. Preferably, the staple should be clinched as much as possible since the fully clinched configuration provides maximum strength.

When the release of the staple has been effected, the user merely has to release lever 32 which causes the actuator blade 34 to move upwardly retracting both the driver and anvil release blades simultaneously. Thus, the subject invention provides for a unique surgical stapler which is simple in construction and may be operated with one hand. The apparatus enables the variable clinching of a staple to facilitate the suturing operation. Further, as the staple is released, the anvil pivots away from the incision permitting the ready removal of the apparatus from the skin without interference. In addition, the arrangement of the apparatus substantially inhibits jamming insuring rapid and smooth operation of the device.

Having disclosed the operation of the subject apparatus, the components thereof will now be described in greater detail. As illustrated in FIGS. 1 and 2, housing 20 of the subject apparatus is generally triangular in configuration. While the triangular configuration offers various advantages, it is to be understood that the subject invention is not intended to be limited thereby. The housing 20 can be made of metal, however, it is preferably formed from a plastic material. More specifically, due to the sterility requirements, it would be desirable to provide a relatively inexpensive plastic apparatus which may be disposed after the operation.

The means for feeding the staples 38 to the lower end of the drive track is enclosed in the lower angled arm portion of the housing. The staple feeding means includes a magazine 40 which can be of any conventional structure and will typically include a pusher plate 66 biased by a spring 68. The staples 38 are generally formed by bending round wire and can have a variety of configurations. The type and amount of clinching is in part determined by the configuration of the staple. In the illustrated embodiment of the subject invention, the crown 42 of the staple 38 has a length substantially greater than the length of the staple legs to facilitate clinching, as more fully described hereinafter.

As illustrated in FIG. 1, anvil 24 is pivotally mounted to housing 20 between a pair of flanges 70 via a pin 72. As illustrated in FIGS. 3 and 5, anvil 24 is generally crescent-shaped and includes a forming lip 46 which projects into the drive track 22. The upper surface of forming lip 46 is preferably planar. The opposed end of anvil 24 includes a locking projection 52 for engagement with the aperture 50 in the driver blade 26. A recess 74 is provided along the side of anvil 24 adjacent the drive track and intermediate the locking projection 52 and the forming lip 46, thereby defining lower edge 48, which facilitates the pivoting of the anvil.

The staples are clinched by downwardly actuating the driver blade 26. Driver blade 26 is mounted in the drive track 22 along channels 80 for reciprocal movement. Driver blade 26 is essentially planar in configuration and includes an aperture 82 adjacent its upper end thereof. Aperture 82 receives the free end 84 of actuator blade 34. As illustrated in FIG. 2, prior to the initiation of the downward stroke of the driver blade, the free end 84 of the actuator blade abuts the upper edge of aperture 82. During the clinching operation, the free end 84 of the actuator blade is biased downwardly into contact with the lower edge of aperture 82, forcing the driver blade downwardly, as illustrated in FIG. 3. After the staple has been ejected (using anvil release blade 28), the lever 32 is released, such that the free end 84 of actuator blade 34 is biased against the upper edge of aperture 82 causing the retracting of the driver blade.

As discussed above, the driver blade 26 includes another aperture 50 disposed intermediate the length thereof. As illustrated in FIG. 2, the lower edge of aperture 50 is in substantial alignment with the locking projection 52 of the anvil at the initiation of the stroke. By this arrangement, after only a small downward movement of the driver blade, the lower edge of aperture 50 is disposed below the locking projection 52 enabling the anvil to partially pivot, as illustrated in FIG. 3.

The pivoting of the anvil causes the locking projection 52 to enter aperture 50 of the driver blade preventing the latter from inadvertently retracting which could result in the jamming of the apparatus. More specifically, in a conventional stapler, removing the downward force on a spring biased driver blade will result in the retraction of the blade. When the driver blade is retracted, the lower end of the driver track is cleared enabling the spring loaded magazine to feed a second staple therein. If the first staple has not yet been ejected from the drive track, two staples will be forced into the drive track simultaneously, frequently causing jamming. Accordingly, it would be desirable to prevent the retraction of the driver blade until the primary staple is released such that no more than one staple will ever be in the drive track at the same time.

This object is achieved in the subject invention due to the interengagement between locking projection 52 and aperture 50 in the driver blade. As pointed out above, the downward force of the driver blade and the staple on the lower edge 48 of the anvil creates a rotational moment tending to pivot the anvil in the direction of arrow B, in FIG. 3. Accordingly, once the bottom edge of aperture 50 is lowered past the locking projection 52, the anvil will pivot such that the locking projection interengages with aperture 50. As long as there is a staple in the drive track, it is impossible for the anvil to return to its initial position. Thus, until the staple is released, the locking projection 52 will remain interengaged with aperture 59 preventing the driver blade from retracting even if an upward biasing force is placed thereon. Once the staple is released from the drive track, the anvil is free to pivot in the opposite direction, enabling the driver blade to retract. Accordingly, the cooperation between the locking projection 52 of the anvil and the aperture 50 in the driver blade prevents the inadvertent retraction of the driver blade thereby substantially inhibiting jamming.

As can be appreciated, when the driver blade moves downwardly, the upper edge of aperture 50 approaches locking projection 52. Accordingly, the length L1 of aperture 50 must be sufficient such that a full downward stroke of the driver blade will not be inhibited by the anvil. In the preferred embodiment of the subject invention, wherein projecting tang 60 is provided on the anvil release blade, the length L1 of aperture 50 must also be sufficient to prevent interference with the tang.

The lower end of driver blade 26 is provided with a configuration which cooperates with forming lip 46 of the anvil to clinch the staples. More particularly, and as illustrated in FIGS. 4 and 6, the staple deforming configuration includes a generally rectangular recess 90 having side edges 92 which flair outwardly. By altering the configuration of the cooperating driver blade-anvil complex and/or the configuration of the staple, the type and extent of the clinching can be varied. In the illustrated example, the forming lip 46 supports the center of the crown 42 of the staple 38, while the outwardly flared sides 92 of recess 90 bear down on the outer edges of the crown. As illustrated in FIG. 4, this action causes the crown 42 of the staple to be bent about points D, thereby inwardly clinching the staple legs. Complete downward actuation of the driver blade results in a fully clinched staple, as illustrated in FIG. 6. Preferably, the lower end of the driver blade is tapered in thickness to insure that only the leading staple is removed from the magazine.

In accordance with the subject invention, anvil release blade 28 is mounted in the drive track 22 behind, and in coplanar relationship with, driver blade 26. Anvil release blade 28 is mounted for reciprocal movement in channels 96. In its retracted position, the lower end of anvil release blade 28 is aligned with the locking projection 52 of anvil 24. By this arrangement, and as illustrated in FIG. 3, the anvil 24 is prevented from fully pivoting until the operator wishes to release the staple. Stated differently, forming lip 46 of the anvil will remain in the drive track 22 for clinching the staple, as long as the anvil release blade 28 is located in its initial upward position such that the lower end thereof is aligned with projection 52 thereby preventing the anvil from pivoting.

Anvil release blade 28 includes an aperture 56 adjacent the lower end thereof. When the operator wishes to release the staple, the anvil release blade is downwardly actuated until aperture 56 is aligned with locking projection 52, as illustrated in FIG. 5. By this arrangement, the anvil is no longer inhibited from pivoting fully, such that forming lip 46 may be withdrawn from the drive track, releasing the staple. The forces acting upon the anvil causing it to pivot are two-fold. As discussed above, the downward force of the driver blade and the staple on the lower edge 48 places a rotational moment on the anvil. In addition, in order to insure that the anvil pivots sufficiently to withdraw the forming lip from the drive track, a projecting tang 60 may be provided on the anvil release blade. Tang 60 which can be formed integrally with the anvil release blade, at the upper edge of aperture 56, projects into aperture 50 of driver blade 26 and is preferably angled upwardly. Thus, as the anvil release blade is actuated downwardly, tang 60 bears upon the upper surface of locking projection 52 urging the anvil to pivot. Preferably, the lower edge of aperture 56 is beveled, as illustrated in FIG. 5, to aid in pivoting the anvil back into its initial position upon the retraction of the anvil release blade.

The upper end of anvil release blade 28 is provided with a second aperture 100. The second aperture 100 is provided to permit the free end 84 of actuator blade 34 to project through the anvil release blade and to be received in aperture 82 of the driver blade. The length L2 of aperture 100 should be sufficient to allow the actuator blade 34 to move downwardly the full extent of its stroke. After the clinching operation is completed, and the driver and anvil release blades are to be retracted, the actuator blade 34 is biased upwardly to its initial position. As the actuator blade moves upwardly, the free end 84 thereof abuts the upper edges of both apertures 82 and 100 in the driver and anvil release blades, respectively, biasing them upwardly into the retracted position.

As illustrated in FIG. 2, the subject surgical stapler 10 is provided with an actuation means which is simple to operate. It is to be understood however, that various other actuation means can be utilized which are within the scope of the subject invention. In the illustrated embodiment, the actuating means includes a handle lever 32 having a modified S shaped configuration. One end 102 of the lever 32 is fixedly connected to a bolt or rivet 104. The opposed end of rivet 104 is fixedly connected to acutator blade 34. Actuator blade 34 is resilient and is preferably formed of spring steel. Interconnecting the upper and lower ends of bolt 104 is a cylindrical pin 106 which passes freely through an aperture 108 in the housing 20. A projection 110 is provided on the lower surface of the housing adjacent the bolt 104 and acts as a fulcrum during the movement of the lever 32.

In order to actuate the driver blade, lever 32 is biased upwardly in a direction of arrow A such that it pivots about fulcrum 110. By this arrangement, the connected end 102 of the lever 32 is moved downwardly in a direction of arrow F, which in turn pulls bolt 104 downwardly therewith. The downward movement of the bolt functions to bias the spring steel actuator blade downwardly. The downward movement of the actuator blade forces the driver blade downwardly as discussed above. The retraction of the driver and anvil release blades is achieved simply by releasing lever 32. The resiliency of the actuator blade 34 causes it to return towards its initial position. The free end 84 of actuator blade bears on the upper edges of apertures 82 and 100 to retract the driver and anvil release blades.

In summary, there has been provided a new and improved surgical stapling apparatus 10 particularly suited for suturing the skin. The subject apparatus includes a housing 20 having an elongated drive track 22 and a means for feeding staples to the lower end thereof. An anvil 24, having a generally crescent-shaped configuration is pivotally mounted adjacent the lower end of the drive track. The anvil includes a forming lip 46 disposed in the drive track. A locking projection 52 is disposed at the opposed end of the anvil to inhibit the jamming of the device. A driver blade 26 and an anvil release blade 28 are reciprocally mounted in coplanar relationship within the drive track. In operation, upon downward actuation of the driver blade, the lower end thereof cooperates with the forming lip of the anvil to deform the staple. The staple is released from the drive track by downwardly actuating the anvil release blade such that an aperture provided therein is aligned with an aperture in the driver blade enabling the anvil to pivot. By this arrangement, the forming lip is retracted from the drive track permitting the release of the deformed staple. The anvil release blade may be actuated during any portion of the clinching operation to attain variable clinching of the staple. The subject surgical apparatus is simple in construction and includes a forming anvil which pivots out of the drive track away from the patient's skin. The device may be simply and rapidly operated with one hand. Further, jamming of the device is substantially inhibited insuring continuous, trouble-free operation.

It is to be understood that while the invention has been described with reference to a preferred embodiment, various changes and modifications may be made therein, by one skilled in the art, without varying from the scope or spirit of the subject invention as defined by the appended claims.

What is claimed is:

1. A surgical apparatus for suturing skin with deformable staples comprising:

a housing having an elongated drive track with one end thereof adapted to be placed against the skin;

means for feeding staples to said drive track at a point adjacent said one end;

anvil means of generally crescent-shaped configuration having opposed ends, with one end thereof including a forming member and with the remaining end thereof including a locking projection, said anvil means being pivotally mounted to said housing, adjacent said one end of said drive track with said forming member extending into said drive track;

an elongated anvil release element mounted for reciprocal movement in said drive track above said anvil means, and with the lower end thereof including an aperture disposed adjacent to and above said locking projection of said anvil means; and an elongated driver element mounted for reciprocal movement in said drive track and disposed over said staple and in coplanar relationship with said anvil release element, said driver element being interposed between said anvil means and said anvil release element, said driver element including an aperture disposed above said locking member of said anvil means and with the lower end of said driver element including a configuration to aid in deforming said staple such that upon downward actuation of said driver element, the latter bears upon the staple such that it is deformed about said forming member in said drive track and wherein said staple is released from said apparatus by the downward actuation of said anvil release element in a manner such that said apertures in said elements are in register, adjacent said locking projection of said anvil means, thereby enabling said anvil means to pivot, with said locking member being received in said aligned apertures such that said forming member is retracted from said drive track permitting the release of said deformed staple.

2. A surgical apparatus as recited in claim 1 wherein said deforming configuration of said lower end of said driver element is defined by a generally rectangular recess, with the side edges of said rectangular recess being outwardly flared towards the lower end of said driver element.

3. A surgical apparatus as recited in claim 2 wherein the upper surface of said forming member and said anvil means is generally planar and cooperates with said rectangular recess of said driver element for clinching said staples.

4. A surgical apparatus as recited in claim 1 wherein said lower end of said driver blade is tapered in thickness.

5. A surgical apparatus as recited in claim 1 wherein said anvil means includes a recess interconnecting said locking projection and said forming member to facilitate the pivoting of said anvil means.

6. A surgical apparatus as recited in claim 1 wherein said anvil release element further includes a tang extending from the upper edge of said opening therein and projecting into said aperture in said driver blade whereby when said anvil release element is downwardly actuated, said tang functions to facilitate the pivoting of said anvil means.

7. A surgical apparatus as recited in claim 1 wherein the upper end of said anvil release element includes a plunger means to facilitate the downward actuation of said anvil release element.

8. A surgical apparatus as recited in claim 1 further including a means to facilitate the downward actuation of said driver element.

9. A surgical apparatus as recited in claim 8 wherein said actuation means includes an actuator element operatively connected to said driver element such that the downward actuation of said actuator element results in the downward actuation of said driver blade.

10. A surgical apparatus as recited in claim 9 wherein said anvil release blade includes an opening disposed adjacent the upper end thereof and wherein said actuator element extends through said opening and is connected to said driver element.

11. A surgical apparatus as recited in claim 10 wherein said actuation means further includes a lever element, said lever element being connected to said actuator element via a pin means, said lever element being in contact with a fulcrum such that upon the upward actuation of said lever element, said pin means functions to downwardly bias said actuator element which in turn downwardly actuates said driver element.

* * * * *